United States Patent [19]

Geller

[11] E Re. 29,077

[45] Reissued Dec. 14, 1976

[54] TABLET FORMULATION

[75] Inventor: Ehud Geller, King of Prussia, Pa.

[73] Assignee: Ives Laboratories Inc., New York, N.Y.

[22] Filed: Mar. 15, 1976

[21] Appl. No.: 666,559

Related U.S. Patent Documents

Reissue of:

[64] Patent No.: 3,883,647
Issued: May 13, 1975
Appl. No.: 312,469
Filed: Dec. 6, 1972

[52] U.S. Cl. ..... 424/15; 424/362
[51] Int. Cl.[2] ..... A61J 3/10; A61K 9/00
[58] Field of Search ..... 424/15, 362

[56] References Cited

UNITED STATES PATENTS

| | | | |
|---|---|---|---|
| 1,836,604 | 12/1931 | Meyer | 127/30 |
| 3,146,168 | 8/1964 | Battista | 424/362 |
| 3,336,200 | 8/1967 | Krause et al. | 424/19 |
| 3,723,614 | 3/1973 | Langauer | 424/15 |
| D. 91,644 | 3/1934 | Blackstone | D16/3 |
| D.201,497 | 6/1965 | Ninger | D16/3 |
| D.202,467 | 10/1965 | Guilmot | D16/3 |

FOREIGN PATENTS OR APPLICATIONS

| | | |
|---|---|---|
| 1,200,790 | 9/1965 | Germany |
| 352,208 | 9/1937 | Italy |
| 6,614,611 | 4/1967 | Netherlands |

OTHER PUBLICATIONS

Reier et al., J. Pharm. Sci. 55(5): 510–514, (1966), "Microcrystalline Cellulose in Tableting."
Reier, Dissertation Abstr. 25(5): 2933 (1964), "Microcrystalline Cellulose in Tableting."
Fox et al., Cosmetic Ind. 92: 161–164, 258–261, (1963), "Microcrystalline Cellulose in Tableting."
Battista et al., Ind. Eng. Chem. 54(9): 20–29, (1962), "Microcrystalline Cellulose."
Woods, Am. Perfumer Cosmet. 80(4): 51–53, 55–60, (1965), "Microcrystalline Cellulose, A New Ingredient for Pharmaceuticals and Cosmetics."

*Primary Examiner*—Shep K. Rose
*Attorney, Agent, or Firm*—Joseph Martin Weigman

[57] ABSTRACT

The disclosure is directed to formulations for tablets which are to be deeply grooved to facilitate breaking into predetermined portions by the user. A critical tablet weight for deeply grooved tablets is disclosed.

6 Claims, 6 Drawing Figures

FIG. 1
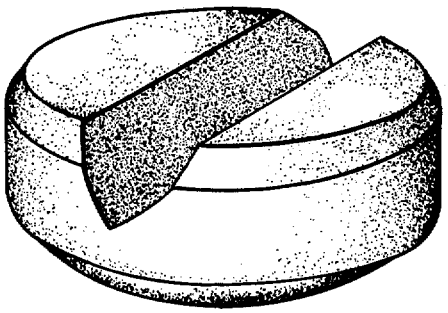
FIG. 2
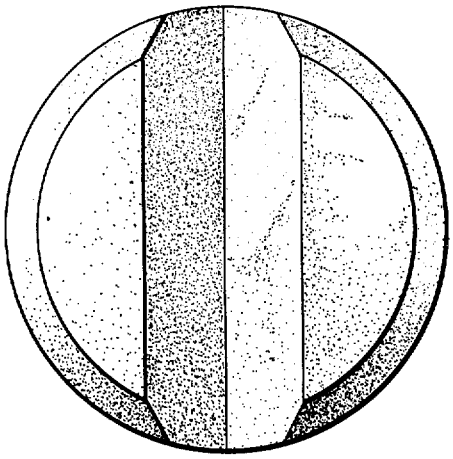
FIG. 3
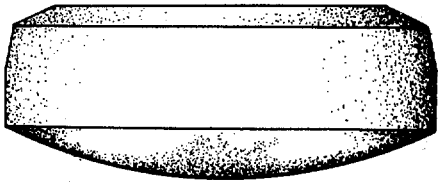
FIG. 4
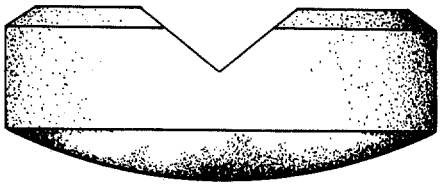
FIG. 5
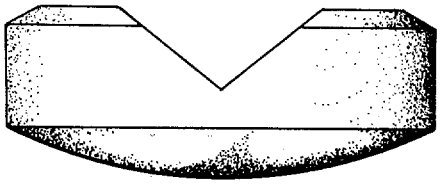
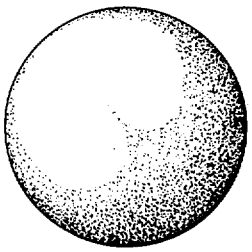
FIG. 6

TABLET FORMULATION

Matter enclosed in heavy brackets [ ] appears in the original patent but forms no part of this reissue specification; matter printed in italics indicates the additions made by reissue.

This invention relates to novel formulations for tablets which are to be deeply grooved. Deeply grooved tablets are those in which the groove is one-third to two-thirds of the total tablet thickness. Such tablets are shown for instance in U.S. Pat. No. 224,591 and in copending applications Ser. No. 386,142 filed Aug. 6, 1973 which is a continuation-in-part of Ser. No. 312,065 filed Dec. 4, 1972 and now abandoned which was in turn a combination of Ser. No. 114,926 filed Feb. 12, 1971 and Ser. No. 124,894 filed Mar. 16, 1971. The foregoing patent and applications were all filed by Edwin F. Roberts and assigned to the assignee of this application. The tablet design allows for easy, simple and accurate division of a pharmaceutical tablet.

In the manufacture of tablets a groove, or bisect, or score, may be formed on one of the tablet faces. The groove facilitates breaking of the tablet into two parts by applying pressure while the tablet is held between two fingers or in both hands.

In the pharmaceutical industry dividing a tablet into two or more accurate predetermined parts permits the administration of two or more doses of the active ingredient, or drug, contained in the tablet. Potent drugs are frequently incorporated in small amounts into a total tablet formulation, and the capability to divide the tablet accurately allows for a saving by not having to formulate, package and distribute different sized tablets for a portion of the dose and for the full dose. In addition, it is often beneficial to the chemical stability of the drug to incorporate the full dose in the smallest tablet size available. The inclusion of one-half of that dose in a tablet of similar size decreases the relation of drug to excipients twofold, thus in many cases also increasing the possibility of drug degradation due to drug-excipient interaction.

Some of the problems that arise in the production of regularly grooved tablets are:

1. Depending on its hardness, it is sometimes impossible to break the tablet although it is scored.

2. Scores do not always assure precise division of the tablet.

3. Pharmaceutical tablets of smaller sizes do not allow for ease of holding and breaking; in which case the patient very often resorts to using other means of dividing the tablet which results in losing parts of it or obtaining uneven parts or both.

Typical deeply scored tablets to which the present invention is applicable are shown in the drawings in which:

FIG. 1 is an isometric view of a pharmaceutical tablet employing a deeply scored design;

FIG. 2 is a top plan view thereof;

FIG. 3 is a side elevational view thereof as seen at right angles to FIG. 2;

FIG. 4 is an end elevational view thereof as seen at right angles to FIG. 2;

FIG. 5 is an end elevational view of a pharmaceutical tablet embodying a modification of the form illustrated in FIG. 4; and FIG. 6 is a bottom view of the embodiments of FIGS. 1 and 5.

The deeply grooved tablet design presents tablet compression characteristics which are not typical of the manufacturing of conventional pharmaceutical tablets. While tablets are usually compacted between uniform surfaces, flat or concave, the deeply grooved tablet design presents a non-uniform compressing surface on one tablet face and a uniform face, spherical or flat, on the other. Such a multiplanar surface presents a process of physical compaction which does not produce the results expected from a conventional compressed tablet. In the process of compaction, the multiplanar surface applies forces, the resultant of which is not vertical. This results in non-uniform stress distribution within the tablet as an independent unit which in turn causes tablet capping and the inadequate imprinting or embossing of indicia of any of its surfaces. In addition, the uneven distribution of stresses results in varying levels of lubrication effectivenss of the tablet planes in contact with the press tooling which, in turn, causes "picking" of material off the tablet surface. To overcome this phenomenon requires a highly cohesive mixture which is at the same time sufficiently lubricated to enable friction-free tooling to tablet contact on all tablet planes. In practice the tablet formulator has to balance the lubricant level against the binder level because the increase of the former will diminish the effect of the latter until the critical region of such action is surpassed.

"Picking" and "sticking" are words of art, meaning part of the tablet sticks to the tips of the upper or lower punch. "Capping" describes a condition in which the tablet laminates into one or more layers.

This invention has been directed principally to the application of specific pharmaceutical formulations incorporating isosorbide dinitrate as the active ingredient, but is applicable to other deeply grooved tablets as well. Isosorbide dinitrate is a potent coronary vasodilator.

It was originally presumed that existing, acceptable, direct compression, tableting compositions could be adequately compressed with deep scoring tooling. Two such compositions were evaluated and surprisingly, it was found that acceptable tablets could not be made. Using a placebo composition (one without an active ingredient) similar to a presently used acceptable isosorbide dinitrate tablet composition, it was determined that, unexpectedly, a total tablet weight was critical to obtain acceptable tablets. To minimize the problems caused by stress non-uniformity, an optimal weight was found where after sufficient compression the distance between the apex of the convex side of the tablet and the bottom of the V-shaped opening on top will be minimal while still allowing for adequate manufacturability.

Having established the critical tablet weight, it was expected that compositions containing the active ingredient would tablet in an acceptable manner because acceptable tablets could be made at this composition using conventional tools. However, unexpectedly, it was found that a critical binder-lubricant relationship was needed to produce acceptable tablets with deep scoring tooling.

Four experiments were designed to select the most optimal tablet weight for the easy-break design. The data is shown in Example I.

EXAMPLE I

TOTAL TABLET WEIGHT OPTIMIZATION

All experiments were run in duplicates from one stock powder mixture and directly compressed on a rotary tablet press. The material run was an optimal placebo mixture as described below:

| FORMULAE | A | B | C | D |
|---|---|---|---|---|
| Lactose hydrous U.S.P. | qs | qs | qs | qs |
| Microcrystalline Cellulose | 25 w/o | 25 w/o | 25 w/o | 25 w/o |
| Magnesium Stearate U.S.P. | 0.25 w/o | 0.25 w/o | 0.25 w/o | 0.25 w/o |
| Total Table Weight | 230 mg | 200 mg | 175 mg | 150 mg |

The pharmaceutical term "qs" is an abbreviation of the Latin phrase quantum sufficiat which means as much as suffices. The abbreviation "w/o" means percent by weight.

The results were as follows:

FORMULA A: Exhibits capping, high friability, in the ranges of 7–15 Strong Cobb units (s.c.u.) hardness; the friability was 2–5% by Roche friabilator.

FORMULA B: Repeated the behavior of Formula A on a somewhat reduced scale.

FORMULA C: Produced satisfactory tablet hardness of 8–14 s.c.u. and friability of 0.0% at that range.

FORMULA D: Produced satisfactory tablets.

Initially it was tried to utilize a conventional isosorbide dinitrate formula and weight for the easy-break tableting tools. It was expected that the design would perform adequately at a total weight of 230 milligrams (mg). Surprisingly the tablets made at this weight were unsatisfactory, and evidenced capping, high friability in addition to insufficient tablet hardness. An attempt was made to solve the problem by selecting the most adequate tablet weight to achieve better manufacturability, but was unsuccessful.

The weight selection experiments indicated that in order to achieve adequate tableting parameters with deep scoring tooling the tablet weight will have to be under 200 mg. The optimum weight is about 175 mg because at 150 mg there is a high probability of tooling contact which in turn may cause damage to the punch tips.

Once the weight problem was solved, no further problems were anticipated. However, upon careful scrutiny of the tableting performance there was found an unexpected problem in the binder and lubricant relationship. "Picking" and "sticking" were found in some cases, and soft tablets with capping in others. In order to resolve the problem a set of experiments was designed to determine the critical nature of the binder and lubricant levels. The experiments are shown in Example II:

EXAMPLE II

Following the procedure of Example I a series of formulations were prepared and deeply scored tablets were made from them. The formulations are shown in Table I.

TABLE I

| FORMULA | PERCENT OF TOTAL TABLET WEIGHT | | | | | | | | | | |
|---|---|---|---|---|---|---|---|---|---|---|---|
| | A | B | C | D | E | F | G | H | I | J | K |
| Microcrystalline Cellulose | 25 | 25 | 25 | 25 | | 45 | 45 | 25 | 25 | 25 | 60 |
| *Solka-floc | | | | | | | | 10 | | | |
| Lactose hydrous | qs | | qs | qs | qs | qs | qs | qs | qs | qs | qs |
| Lactose, anhydrous | | 63 | | | | | | | | | |
| Dicalcium Phosphate | | | | | | | | | | | |
| **Sta-Rx 1500 | | | | | 74 | | | | | | |
| Magnesium Stearate | 0.22 | 0.3 | 0.22 | 0.22 | 0.3 | 0.22 | 0.35 | 0.3 | 0.3 | 0.4 | 0.35 |
| Stearic Acid | | | | | | | | | | | |
| ***Stero-Tex | | | 0.50 | | | | | | | | |
| Talc | | | | 2 | | | | | | | |
| Isosorbide Dinitrate Trituration | 20.0 mg | 20.0 mg | 20.0 mg | 20.0 mg | 20.0 mg | 20.0 mg | 20.0 mg | 20.0 mg | 20.0 mg | 20.0 mg | 20.0 mg |
| Total Weight mg | 175 | 175 | 175 | 175 | 175 | 175 | 175 | 175 | 175 | 175 | 175 |

Formulaes A through H with the exception of G did not exhibit adequate manufacturability in a direction compression process.
*Purified Cellulose, Brown Co.
**Directly compressible starch
***Edible vegetable oil, powdered lubricant Shown in Table I are drug amounts of 20 mg/tablet each. These correspond to a tablet containing 5 mg. of isosorbide dinitrate which is utilized in a 25 weight percent mixture with lactose being 75 weight percent. To prepare a 10 mg. isosorbide dinitrate tablet 40 mg. of drug-lactose mixture would be used (representing 10 mg. of isosorbide dinitrate). The change in dosage is balanced with the amount of lactose in the formulation while producing similar results.

The results were as follows:

FORMULA A exhibited severe picking on the upper face of the tablet.

FORMULA B contained the minimal level of anhydrous lactose to produce an adequate tablet. However, the tablet demonstrated poor disintegration.

FORMULA C produced soft tablets that capped while still picking.

FORMULA D exhibited insufficient hardness range and picking on both tablet faces.

FORMULA E showed insufficient binding resulting in very soft tablets having high friability.

FORMULA F showed inadequate performance because of slight pick.

FORMULA G showed adequate manufacturability as to hardness and friability. The tablets were free of picking.

FORMULA H showed insufficient hardness with picking on bottom face.

FORMULA I was a slugged formula which exhibited binding and picking on the tablet lower face.

FORMULA J was a slugged formula with a higher lubricant level which produced adequate lubrication but insufficient hardness.

FORMULA K showed excellent manufacturability for all parameters.

Based on the foregoing it was determined that tablets made of conventional pharmaceutical ingredients would manufacture adequately at weights under 200 mg. utilizing a deeply scored design. In addition, a great amount of experimentation and design was spent on the tablet formulation to overcome the critical nature of its binder and lubricant dependence.

From the foregoing the preferred weight for deeply grooved tablets is 150 to 175 mg. The preferred ratio of lubricant to binder is obtained when the binder constitutes 45 to 99.7 w/o and the lubricant constitutes 0.3 to 0.4 w/o of tablet exclusive of the amount of the active ingredient, fillers, extenders, flavor and the like. That is, the weight per cent of the binder and lubricant is based on the portion of the tablet composition usually referred to as q.s.

Only microcrystalline cellulose of the binders presently available on the market has been found to be useful in deep grooved tablet compositions. Only the stearates, including stearic acid, of the lubricants presently available on the market have been found to be useful in deep grooved tablet compositions.

A particularly advantageous formula weighs 175 mg. per tablet and contains 60 percent by weight microcrystalline cellulose with 0.35 percent by weight of magnesium stearate.

For assuring of disintegration and dissolution reproducibility the use of 1 percent Amberlite is optional and has been tested to that effect.

EXAMPLE III

Preparation of 10 mg. Isosorbide Dinitrate Chewable Tablets

The deeply scored design was also utilized in the manufacture of a chewable tablet form containing isosorbide dinitrate at a 10 mg. level.

Again, in this formula it was found necessary to resort to a lower tablet weight of 175 mg. In addition, because the design of a chewable tablet requires the incorporation of a chewable carrier, it was necessary to evaluate different chewable materials to obtain a sufficiently cohesive and well lubricated direct compression formula. The data obtained in those experiments is shown in Table II in which the tablets were prepared as described in Example I.

TABLE II

| FORMULAE | CHEWABLE TABLETS A | B | C | D | E | F | G | H |
|---|---|---|---|---|---|---|---|---|
| Isosorbide Dinitrate (25%) | 40 mg | 40 mg | 40 mg | 40.0 mg | 40 mg | 40 mg | 40.0 mg | 40.0 mg |
| Lactose mixture *Nutab | qs | qs | | | | | | |
| Mannitol U.S.P. | | | qs | 20% | 20% | 20% | qs | |
| **Cellutab, anhydrous | | | | 31.5% | 31.5% | 31.5% | | qs |
| Microcrystalline Cellulose | 25.0% | 20% | | 25% | 25% | 25% | 25% | 20% |
| Solka floc | | 8.0% | | | | | | |
| Magnesium Stearate U.S.P. | 0.6% | 0.7% | 1.0% | 1.0% | 0.5% | 0.9% | 0.9%+0.9% | 0.35% |
| FD&C Yellow No. 5 Lake | 0.1% | 0.1% | 0.4% | 0.4% | 0.4% | 0.4% | 0.4% | 0.4% |
| Sodium Saccharine N.F. | | | 0.08% | 0.08% | 0.08% | — | 0.08% | — |
| Methyl Cellulose 400 cps | | | .07% | | | | | |
| Lemon Oil, spray dried | | | 1.7% | 1.7% | 1.7% | 1.7% | 1.7% | |
| | | | | | 1.7% | | | |
| Total Tablet Weight | 222.5 mg | 196 mg | 190 mg | 175.0 mg | 175 mg | 175 mg | 175.0 mg | 175 mg |

*Sucrose, invert sugar, starch, magnesium stearate direct compression granulation.
**Dextrose and corn syrup solids granulation.

Formulae A, B, D, E and F are directly compressed.

Formula A exhibited very high friability, capping and a narrow hardness range.

In Formula B the weight has been reduced, but tablets still exhibit heavy capping and friability with very low hardness.

Formula C was a wet granulated formula, and exhibited high friability, capping and inadequate chewability due to the wet binder.

Formula D shows adequate manufacturability and chewability.

In Formula E reduced lubricant level results in heavy picking on both tablet faces.

In Formula F eliminating the sweetener from Formula D maintains adequate manufacturability with improved taste.

Formula G was slugged and exhibited capping, narrow hardness range and slight picking.

Formula H produced adequate tableting characteristics.

From the foregoing it was concluded that 10 mg. chewable tablets were successfully made in two formulations:

1. The first formulation uses a directly compressed mannitol and a dextrose and corn syrup solids granulation in combination;
2. The second formulation uses dextrose and corn syrup solids granulation without mannitol in direct compression.

The choice between these two categories depends strictly on personal taste preference. Both formulae will produce similarly adequate results.

The preferred embodiment at which chewable deeply scored tablets can be made is for the first category with at least 20 percent by weight of microcrystalline cellulose, 31.5 percent by weight of Cellutab anhydrous, 25 percent mannitol and a range of 0.7–1.0 percent by weight of magnesium stearate or: at the second category with Cellutab anhydrous and a minimum of 0.35 percent by weight of magnesium stearate.

The incorporation of an ingredient which would serve as a chewable carrier, one which imparts a certain pallatable feeling, sweetness and desirable chewability, presents additional variables to the ones already described above. When processing and formulating for such purpose, it is necessary to consider the properties producing the resulting chewable quality of the tablet, that is hardness, taste and pallatability. The majority of chewable carriers, apart from the granulated natural sugars and their derivatives, do not lend themselves to direct compression and tend to lose some of their taste upon any granulation method.

The examples illustrated in Table II present the compositions of pharmaceutical tablets manufactured by three basic methods; direct compression, dry granulation, and wet granulation. These examples are not to be construed as limiting the scope of this invention which may only be determined by reference to the appended claims.

What is claimed is:

1. A pharmaceutical tablet which is adequately imprinted with indicia or embossing and scored to form a groove which is one-third to two-thirds the depth of the total tablet thickness to facilitate separation into subdivisions containing substantially equal amounts of a pharmaceutically active ingredient comprising a directly compressed formulation of 5 to 10 milligrams of an active ingredient, the remainder being 45 to 99.7 percent by weight of microcrystalline cellulose and 0.3 to 0.4 percent by weight of magnesium stearate, along with fillers, extenders, flavoring and the like.

2. The tablet as defined in claim 1 in which the total tablet weight is 150 to 175 milligrams.

3. A tablet as defined in claim 1 in which the total tablet weight is about 175 milligrams.

4. A tablet as defined in claim 1 in which the microcrystalline cellulose is present in the amount of 60 percent by weight and the magnesium stearate is present in the amount of 0.35 percent by weight.

5. A tablet as defined in claim 1 in which the active ingredient is 5 to 10 milligrams of isosorbide dinitrate.

*6. A pharmaceutical tablet which is adequately imprinted with indicia or embossing and scored to form a groove which is one-third to two-thirds the depth of the total thickness to facilitate separation into subdivisions containing substantially equal amounts of a pharmaceutically active ingredient comprising a directly compressed formulation of an effective amount of an active ingredient, the remainder being 45 to 99.7 percent by weight of microcrystalline cellulose and 0.3 to 0.4 percent by weight of magnesium stearate, along with fillers, extenders, flavoring and the like.*

* * * * *